(12) United States Patent
Venkataraman et al.

(10) Patent No.: US 7,355,077 B2
(45) Date of Patent: Apr. 8, 2008

(54) PROCESS FOR PREPARING TOLTERODINE

(75) Inventors: Sundaram Venkataraman, Hyderabad (IN); Vijayavitthal Thippannachar Mathad, Hyderabad (IN); Kikkuru Srirami Reddy, Guntur (IN); Neti Srinivasan, Rhimavaram (IN); Chinta Raveendra Reddy, Chittoor (IN); Muthulingam Arunagiri, Hyderabad (IN); Routhu Lalitha Kumari, Hyderabad (IN)

(73) Assignees: Dr. Reddy's Laboratories Limited, Hyderabad (IN); Dr. Reddy's Laboratories, Inc., Bridgewater, NJ (US)

(*) Notice: Subject to any disclaimer, the term of this patent is extended or adjusted under 35 U.S.C. 154(b) by 162 days.

(21) Appl. No.: 11/259,322

(22) Filed: Oct. 26, 2005

(65) Prior Publication Data

US 2006/0094904 A1 May 4, 2006

Related U.S. Application Data

(60) Provisional application No. 60/622,829, filed on Oct. 28, 2004.

(51) Int. Cl.
*C07C 209/16* (2006.01)
*C07C 213/02* (2006.01)
*C07C 211/27* (2006.01)
*C07C 69/76* (2006.01)

(52) U.S. Cl. .................. 564/316; 564/324; 564/396; 564/399; 560/57

(58) Field of Classification Search .............. None
See application file for complete search history.

(56) References Cited

U.S. PATENT DOCUMENTS 5,382,600 A * 1/1995 Jonsson et al. ............. 514/603
5,922,914 A * 7/1999 Gage et al. ................. 564/413
6,822,119 B1 * 11/2004 Kumar et al. ............... 564/316

OTHER PUBLICATIONS

The Merck Index 13$^{th}$ edition (2001), M. J. O'Neil ed., Merck & Co., Inc., Whitehouse Station, NJ, p. 1699, entry No. 9606.*
Database CAPLUS on STN, Acc. No. 2002:51413, Donsbach et al., WO 2002004399 (Jan. 17, 2002) (abstract).*
Database CAPLUS on STN, Acc. No. 1999:736261, Sparf et al., EP 957073 (Nov. 17, 1999) (abstract).*
Database CAPLUS on STN, Acc. No. 1998:682217, Johansson et al., WO 9843942 (Oct. 8, 1998) (abstract).*
Database CAPLUS on STN, Acc. No. 1994:508197, Johansson et al., WO 9411337 (May 26, 1994) (abstract).*

* cited by examiner

*Primary Examiner*—Brian Davis
(74) *Attorney, Agent, or Firm*—Milagros A. Cepeda; Robert A. Franks; Lee Banks

(57) ABSTRACT

A process for preparing tolterodine with high purity.

10 Claims, No Drawings

PROCESS FOR PREPARING TOLTERODINE

CROSS-REFERENCE TO RELATED APPLICATION

This application is a nonprovisional filing of U.S. Provisional Application No. 60/622,829 filed on Oct. 28, 2004, the entire disclosure of which is hereby incorporated by reference.

INTRODUCTION TO INVENTION

The present invention relates to a process for the preparation of tolterodine, and pharmaceutically acceptable salts thereof. More particularly the present invention relates to a process for proficiently preparing substantially pure tolterodine and salts thereof.

Tolterodine has the chemical name (+)-N,N-diisopropyl-3-(2-hydroxy-5-methylphenyl)-3-phenylpropylamine, or (R)-2-[3-[bis(1-methylethyl)amino]-1-phenylpropyl]-4-methylphenol, and can be represented by the following structural Formula I.

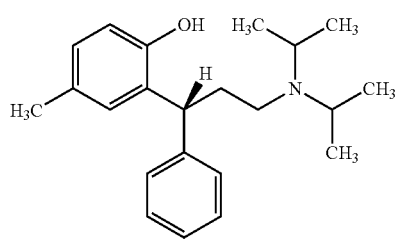

Formula I

Tolterodine is a muscarinic receptor antagonist, useful in the treatment of urinary incontinence and other symptoms of bladder over activity. It is commercially available in products sold under the brand name DETROL™, containing tolterodine tartrate as the active ingredient.

U.S. Pat. No. 5,382,600 discloses tolterodine and its pharmaceutically acceptable salts along with pharmaceutical composition. This patent also describes a process for the preparation of tolterodine that involves the reaction of 3,4-dihydro-6-methyl-4-phenyl-2H-benzopyran-2-one with methyl iodide and potassium carbonate in refluxing acetone/methanol to give methyl-3-(2-methoxy-5-methylphenyl)3-phenyl propionate. The ester thus obtained is reduced with lithium aluminum hydride in ether to the corresponding propanol, which is reacted with tosyl chloride and pyridine to yield the tosylate, which on condensation with diisopropylamine in hot acetonitrile is converted into the tertiary amine. The tertiary amine is treated with boron tribromide in dichloromethane to give the amine of Formula I as a racemic mixture, which is resolved with L-(+) tartaric acid.

Long reaction time and low overall yields makes this process very expensive and less productive. Furthermore, the use of expensive and hazardous reagents like methyl iodide, lithium aluminum hydride, and boron tribromide also renders this process unsuitable and hazardous on a commercial scale.

U.S. Pat. No. 5,922,914 provides an alternate method for the preparation of tolterodine. The process involves the cyclization of trans-cinnamic acid with p-cresol in hot sulfuric acid to give 3,4-dihydro-6-methyl-4-phenyl-2H-benzopyran-2-one, which is reduced with diisobutyl aluminum hydride (DIBAL) in toluene to yield 6-methyl-4-phenyl-3,4-dihydro-2H-1-benzopyran-2-ol. This on reducto-condensation with diisopropylamine, by means of hydrogen over palladium on charcoal in methanol, affords racemic tolterodine of Formula I, which is resolved with L-(+)-tartaric acid.

This process is also not commercially feasible since it makes use of an expensive and hazardous reagent DIBAL. Although the numbers of steps are reduced, the cost incurred to produce tolterodine is high.

U.S. Pat. No. 6,822,119 provides another alternate method for the preparation of tolterodine. The process involves reacting 3,4-dihydro-6-methyl-4-phenyl-2H-benzopyran-2-one with dimethyl sulphate in the presence of sodium hydroxide, and a phase transfer catalyst to obtain methyl-3-(2-methoxy-5-methylphenyl)-3-phenyl propionate. Reducing the ester thus obtained with a reducing agent in the presence of a Lewis acid to obtain 3-(2-methoxy-5-methylphenyl)-3-phenyl propanol. Protecting the hydroxy group of the alcohol to followed by aminating with diisopropylamine to give N,N-diisopropyl-3-(2-methoxy-5-methylphenyl)-3-phenylpropylamine and removing the hydroxy protecting group to obtain N,N-diisopropyl-3-(2-hydroxy-5-methylphenyl)-3-phenylpropylamine of Formula I.

This process involves a large number of steps and isolation of intermediates at each step, leading to poor yields.

International Publication WO 2004/078700 describes preparation of pure tolterodine or a pharmaceutically acceptable salt thereof and a pharmaceutical composition containing the same. It also discloses N,N-di-[3-[2-hydroxy-5-methylphenyl]-3-phenylpropyl]isopropyl amine, referred to as "tolterodine dimer," and a process for isolation of the same.

Consequently, there is a long-felt need for a process for the preparation tolterodine which not only overcomes the problems in the art processes as mentioned above, but is also safe, cost effective, and industrially feasible.

SUMMARY OF THE INVENTION

The present invention, in one aspect, relates to a process for the preparation of tolterodine of Formula I, and pharmaceutically acceptable salts thereof, comprising the steps of:

a) reaction of 6-methyl-4 phenyl-3,4-dihydrocoumarin of Formula II with a benzyl halide in the presence of a suitable base in a suitable solvent to give methyl-3-(2-benzyloxy-5-methylphenyl)-3-phenylpropionate of Formula III;

b) reduction of methyl-3-(2-benzyloxy-5-methylphenyl)-3-phenylpropionate of Formula III with a suitable reducing agent in a suitable solvent to get 3-(2-benzyloxy-5-methylphenyl)-3-phenylpropanol of Formula IV;

c) protection of the hydroxy group of 3-(2-benzyloxy-5-methylphenyl)-3-phenylpropanol of Formula IV in the presence of a suitable base in a suitable solvent to give the compound of Formula IVa;

d) amination of the compound of Formula IVa with diisopropylamine in the presence of a suitable solvent to obtain N,N-diisopropylamine-3-(2-benzyloxy-5-methylphenyl)-3-phenylpropylamine of Formula IVb e) debenzylation of the compound of Formula IVb with a suitable reagent in a suitable solvent to give N,N-diisopropyl-3-(2-hydroxy-5-methylphenyl)-3-phenylpropylamine hydrochloride of Formula V; and f) converting the compound of Formula V into the compound of Formula I and, optionally, into a pharmaceutically acceptable salt thereof.

Suitably, one or more sequential steps a) to f) are carried out without isolating intermediate compounds. In one embodiment of the invention, steps c), d), and e) are carried out without isolating intermediates, followed by isolation of the compound of Formula V.

In another aspect, the present invention provides substantially pure tolterodine tartrate and a process for preparation thereof. In an embodiment, tolterodine tartrate of the present invention contains low concentration of any one or more of the following:
a) bis-[3-(2-benzyloxy-5-methyl-phenyl)-3-phenyl-propyl]-isopropyl-amine;
b) 2-(3-{[3-(2-Benzyloxy-5-methyl-phenyl)-3-phenyl-propyl]-isopropyl-amino}-1-phenyl-propyl)-4-methyl-phenol; and
c) [3-(2-Benzyloxy-5-methyl-phenyl)-3-phenyl-propyl]-isopropyl-amine.

In yet another aspect, the present invention provides compounds of Formulae III, VI, VII, and VIII.

In a further aspect, the present invention provides process for the preparation of the compounds of Formulae III, VI, VII, and VIII.

DETAILED DESCRIPTION

The present invention, in one embodiment, relates to a process for the preparation of tolterodine of formula I and pharmaceutically acceptable salts thereof, comprising the steps of:
a) reaction of 6-methyl-4 phenyl-3,4-dihydrocoumarin of Formula II

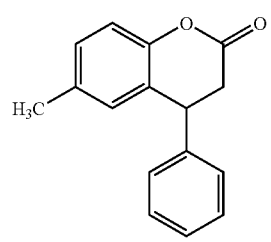

Formula II with a benzyl halide in the presence of a suitable base in a suitable solvent to give methyl-3-(2-benzyloxy-5-methylphenyl)-3-phenylpropionate of Formula III;

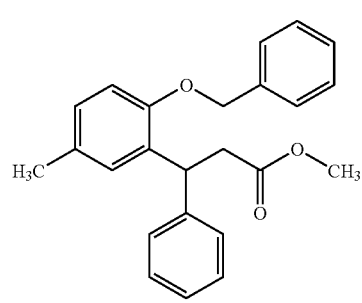

Formula III b) reduction of methyl-3-(2-benzyloxy-5-methylphenyl)-3-phenylpropionate of Formula III with a suitable reducing agent in a suitable solvent to get 3-(2-benzyloxy-5-methylphenyl)-3-phenylpropanol of Formula IV;

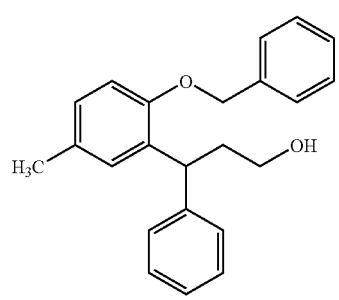

Formula IV c) protection of the hydroxy group of 3-(2-benzyloxy-5-methylphenyl)-3-phenylpropanol of Formula IV in the presence of a suitable base in a suitable solvent to give the protected compound of Formula IVa, where "Ts" represents a tosyl group according to one embodiment;

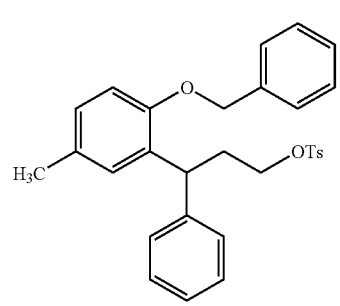

Formula IVa d) amination of the compound of Formula IVa with diisopropylamine in the presence of a suitable solvent to obtain N,N-diisopropylamine-3-(2-benzyloxy-5-methylphenyl)-3-phenylpropylamine of Formula IVb

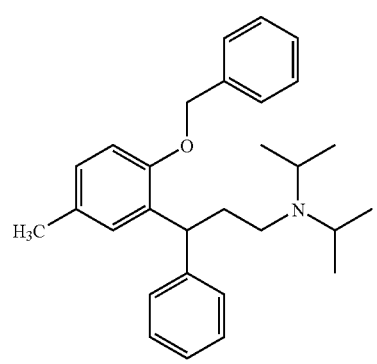

Formula IVb e) debenzylation of the compound of Formula IVb with a suitable reagent in a suitable solvent gives N,N-diisopropyl-3-(2-hydroxy-5-methylphenyl)-3-phenylpropylamine hydrochloride of Formula V; and

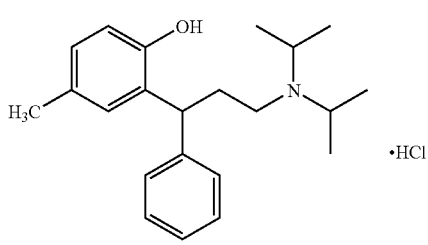

Formula V f) converting the compound of Formula V into the tolterodine compound of Formula I by reacting with a base and subsequently, if desired, forming a pharmaceutically acceptable salt.

Step a) involves reaction of 6-methyl-4 phenyl-3,4-dihydrocoumarin of Formula II with a benzyl halide in the presence of a suitable base in a suitable solvent to give methyl 3-(2-benzyloxy-5-methylphenyl)-3-phenylpropionate of Formula III.

Benzyl halides that can be used in the reaction include benzyl bromide, benzyl chloride, and the like.

Suitable solvents that can be used in the reaction include, but are not limited to: alcohols such as methanol, ethanol, propane, butanol, and the like; ketones such as acetone, ethyl methyl ketone, methyl Isobutyl ketone, and the like; esters such as ethyl acetate, propyl acetate, and the like; and mixtures thereof.

Suitable bases that can be used in the reaction include, but are not limited to: hydroxides of alkali metals such as lithium hydroxide, sodium hydroxide, potassium hydroxide, and the like; carbonates of alkali metals such as sodium carbonate, potassium carbonate, and the like; and bicarbonates of alkali metals such as sodium bicarbonate, potassium bicarbonate, and the like; and organic bases such as triethylamine, tributylamine, tripropyl amine, and the like.

A suitable temperature for conducting the reaction can range from 20-100° C., or 30-75° C., or at the reflux temperature of the solvent used.

Step b) involves reduction of methyl 3-(2-benzyloxy-5-methylphenyl)-3-phenylpropionate of Formula III with a suitable reducing agent in a suitable solvent to get 3-(2-benzyloxy-5-methylphenyl)-3-phenylpropanol of Formula IV.

Suitable reducing agents used in the reaction include, but are not limited to, VITRIDE®, also known as "SDMA," a 65% solution of sodium dihydro-bis-(2-methoxy ethoxy) aluminate in toluene, sold by Chematek S.P.A. Chemical Products, Italy, and the like.

Suitable solvents that can be used in the reaction include any solvent or mixture of solvents, in which the required components are soluble. Examples include, without limitation thereto: ethers such as diethyl ether, dimethyl ether, di-isopropyl ether, methyl tertiary-butyl ether, tetrahydrofuran, 1,4-dioxane, and the like; aliphatic hydrocarbons such as $C_1$-$C_{10}$ straight chain or branched hydrocarbons, and the like; aromatic hydrocarbons such as toluene, xylene, and the like; and mixtures thereof.

Suitable temperatures for conducting the reaction can range from 0-70° C., or 10-50° C., or 20-40° C.

Step c) involves protecting the hydroxy group of 3-(2-benzyloxy-5-methylphenyl)-3-phenylpropanol of Formula IV in the presence of a suitable base in a suitable solvent to give the compound of Formula IVa.

Suitable protecting agents that can be used in step c) include those providing alkyl or arylsulfonyloxy groups, such as methane sulphonyl chloride, benzene sulphonyl chloride, p-toluene sulphonyl chloride, and the like;

Suitable bases that can be used in the reaction include, but are not limited to: hydroxides of alkali metals such as lithium hydroxide, sodium hydroxide, potassium hydroxide, and the like; carbonates of alkali metals such as sodium carbonate, potassium carbonate, and the like; and bicarbonates of alkali metals such as sodium bicarbonate, potassium bicarbonate, and the like; and organic bases such as triethylamine, tributylamine, tripropyl amine, and the like.

Suitable solvents that can be used in the reaction include any solvent or mixture of solvents, in which the required components are soluble. Examples include: halogenated solvents such as dichloromethane, 1,2-dichloroethane, chloroform, and the like; ketones such as acetone, ethylmethyl ketone, methylisobutyl ketone, and the like; esters such as ethyl acetate, n-propyl acetate, n-butyl acetate, t-butyl acetate, and the like; ethers such as diethyl ether, dimethyl ether, di-isopropyl ether, methyltertiarybutyl ether, tetrahydrofuran, 1,4-dioxane, and the like; hydrocarbons such as toluene, xylene, and the like; nitriles such as acetonitrile, propionitrile, and the like; and mixtures thereof in various proportions.

Suitable temperatures for conducting the reaction can range from 0-70° C., or 10-50° C., or 25-35° C.

The intermediate compound of Formula IVa in step c) may or may not be isolated. The same can be converted in situ, if desired, to the compound of Formula IVb in step d).

Step d) involves amination of the compound of Formula IVa with diisopropylamine in the presence of a suitable solvent to obtain N,N-diisopropylamine-3-(2-benzyloxy-5-methylphenyl)-3-phenylpropylamine of Formula IVb.

Suitable solvents that can be used in the reaction include any solvent or mixture of solvents, in which the required components are soluble. Examples include ketones such as acetone, ethylmethyl ketone, methylisobutyl ketone, and the like; esters such as ethyl acetate, n-propyl acetate, n-butyl acetate, t-butyl acetate, and the like; ethers such as diethyl ether, dimethyl ether, di-isopropyl ether, methyltertiarybutyl ether, tetrahydrofuran, 1,4-dioxane, and the like; hydrocarbons such as toluene, xylene, and the like; nitrites such as acetonitrile, propionitrile, and the like; and mixtures thereof in various proportions.

Suitable temperatures for conducting the reaction can range from 50-130° C., or 75-120, or 110-115° C., optionally in a closed reactor so that internal pressure will be developed, which pressures typically can range up to 5 kg/cm², or 1-4 kg/cm² or 2-3 kg/cm².

The intermediate compound of Formula IVb in step d) may or may not be isolated. The same can be converted in situ, if desired, to the compound of Formula V in step e).

Step e) involves debenzylation of the compound of Formula IVb with a suitable reagent in a suitable solvent to give N,N-diisopropyl-3-(2-hydroxy-5-methylphenyl)-3-phenylpropylamine hydrochloride of Formula V.

Suitable debenzylating reagents that can be used in the reaction include, but are not limited to, a noble metal catalyst such as nickel, palladium, platinum, iridium, ruthenium and the like, in combination with hydrogen.

Suitable solvents that can be used in the reaction include any solvent or mixture of solvents, in which the required components are soluble. Examples include $C_1$-$C_6$ straight chain or branched alcohols such as methanol, ethanol, isopropanol, butanol and the like; hydrocarbons such as toluene, xylene, and the like; or mixtures thereof.

Step f) involves conversion of the compound of Formula V into the tolterodine compound of Formula I and subsequent formation of any desired pharmaceutically acceptable salts thereof.

The pharmaceutically acceptable salts include, but are not limited to, hydrochloride, hydrobromide, hydrogen sufate, tosylate, fumarate, maleate, tartarate methane sulfonate, and the like.

Suitable solvents that can be used in the reaction include any solvent or mixture of solvents having the required solubility parameters. Examples include: $C_1$-$C_6$ straight chain or branched alcohols such as methanol, ethanol, isopropanol, butanol, and the like; halogenated hydrocarbons such as dichloromethane, 1,2-dichloroethane, chloroform, and the like; ketones such as acetone, ethylmethyl ketone, methylisobutyl ketone, and the like; esters such as ethyl acetate, n-propyl acetate, n-butyl acetate, t-butyl acetate, and the like; ethers such as diethyl ether, dimethyl ether, di-isopropyl ether, methyltertiarybutyl ether, tetrahydrofuran, 1,4-dioxane, and the like; hydrocarbons such as toluene, xylene, and the like; nitriles such as acetonitrile, propionitrile, and the like; and mixtures thereof in various proportions.

The whole process can be represented by the following reaction scheme A.

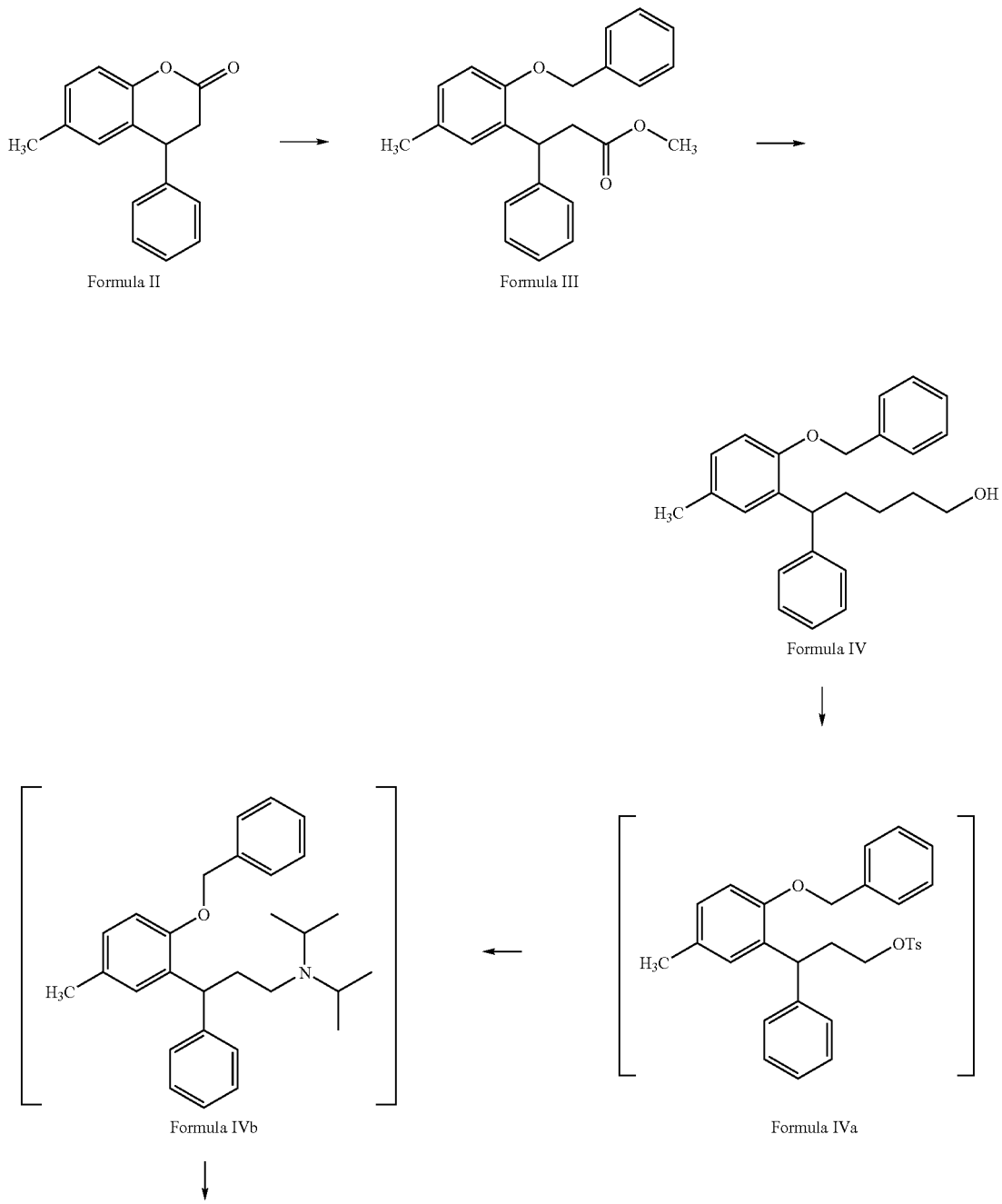

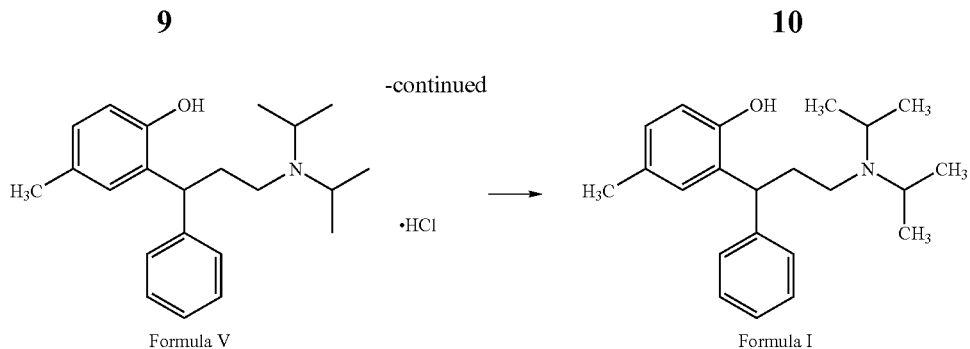

Formula V → Formula I

In another aspect, the present invention provides substantially pure tolterodine tartrate and a process for preparation thereof.

Tolterodine tartrate prepared according to this embodiment has a low level of impurities, as determined by high performance liquid chromatography ("HPLC"). For example, it contains about 0.15 area-%, or 0.05 area-%, or less, of any of the following impurities:

a) bis-[3-(2-benzyloxy-5-methyl-phenyl)-3-phenyl-propyl]-isopropylamine of Formula VI;
b) 2-(3-{[3-(2-Benzyloxy-5-methyl-phenyl)-3-phenyl-propyl]-isopropyl-amino}-1-phenyl-propyl)-4-methylphenol of Formula VII; and
c) [3-(2-Benzyloxy-5-methyl-phenyl)-3-phenyl-propyl]-isopropylamine of Formula VIII.

In yet another aspect, the present invention provides compounds having Formulae III, VI, VII, and VIII.

Formula III

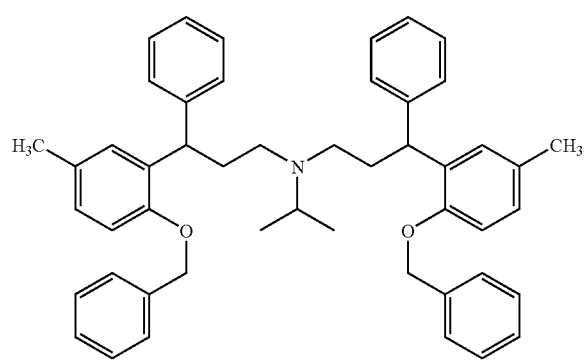

Formula VI

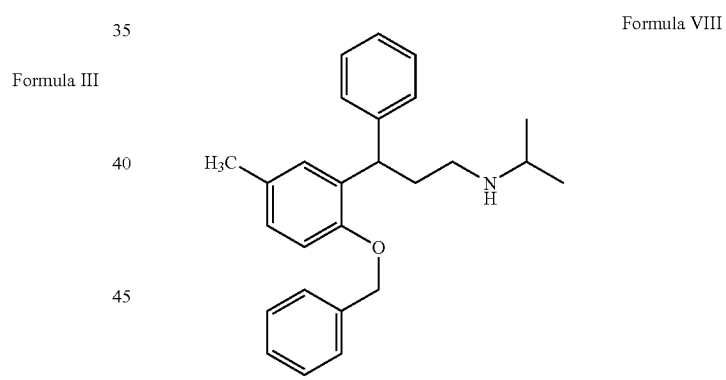

Formula VII

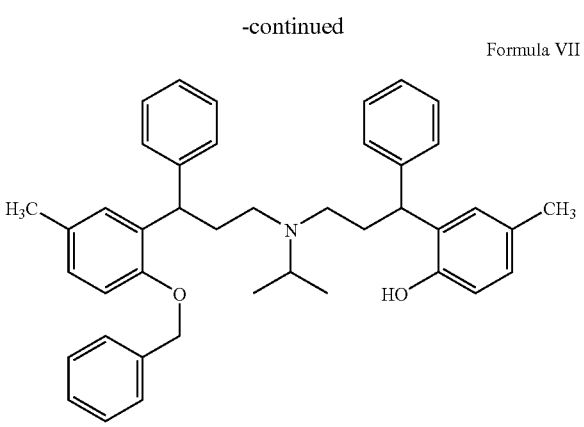

Formula VIII

In still further aspect, the present invention provides processes for preparing the compounds of Formulae III, VI, VII, and VIII.

The processes described herein are further described in the following examples. These examples are provided solely for the purpose of illustrating certain aspects and embodiments of the invention, and therefore should not be construed as limiting the scope of the invention.

EXAMPLE 1

Preparation of METHYL 3-(2-BENZYLOXY-5-METHYLPHENYL)-3-PHENYLPROPIONATE (Formula III)

675 g of 6-methyl-4 phenyl-3,4-dihydrocoumarin, 372 ml of benzyl bromide, and 513 g of potassium carbonate were charged into a round bottom flask containing a mixture of 2025 ml of acetone and 2025 ml of methanol. The contents were heated to reflux temperature for about 2-3 hours. Distilled off the solvent from the reaction mass at atmospheric conditions below 75° C. then under vacuum (about 600 mm Hg) at below 85° C. 6750 ml of water was added to the residue and stirred for 15 minutes for dissolution. Extracted the solution twice with ethyl acetate (4000 ml). Combined organic layers were washed with water (2×3375 ml) and distilled the solvent under vacuum (about 600 mm Hg) at below 85° C. 2025 ml of methanol was added to the residue at 50-55° C., then stirred the solution at 0-5° C. for about 2 hours. Filtered the formed solid and washed with 675 ml of methanol. Dried the solid at 50-55° C. for about 2-3 hours under vacuum (about 600 mm/Hg) to get 850 g of the title compound.

$^1$H NMR (200 MHz, CDCl$_3$, δ in ppm): 2.25 (s, 3H), 3.05 (d, J=3.4, 2H), 3.50 (s, 3H), 4.95 (t$_e$, 1H), 4.95 (s$_e$, 2H), 6.6-7.4 (m, Ar—H, 13H). Mass: m/z 360.

EXAMPLE 2

Preparation of
3-(2-BENZYLOXY-5-METHYLPHENYL)-3-PHENYLPROPANOL (Formula IV)

810 g of methyl-3 -(2-benzyloxy-5-methylphenyl)-3 -phenylpropionate and 3240 ml of toluene were stirred at 25-30° C. for about 20 minutes. 842.5 ml of VITRIDE® (sodium bis(2-methoxyethoxy)aluminum hydride, 65% w/w in toluene) was added slowly to the reaction mass below 40° C. under a nitrogen atmosphere, and stirred for about 20-25 minutes. A solution of 1620 ml of concentrated hydrochloric acid and 1620 ml of water was added slowly to the reaction mass and stirred for 15-20 minutes. The aqueous layer was separated and extracted with toluene (810 ml). Combined organic layers were washed with 4050 ml of water and then with 10% aqueous sodium carbonate solution (4050 ml). Organic layer was further washed with water (2×2430 ml) and the solvent was distilled under vacuum (about 600 mm Hg) below 100° C. 3240 ml of hexane was added to the residue at 30-40° C. and stirred for 2-3 hours. It was further cooled to 20-25° C. and stirred for 2-3 hours. Filtered the solid and washed with hexane (810 ml). Dried the solid at 25-30° C. under vacuum (about 600 mm Hg) for 2-3 hours to get 680 g of the title compound.

$^1$H NMR (200 MHz, CDCl$_3$, δ in ppm): 1.60 (s, 1H), 2.25 (s, 3H), 2.30 (q, J=10.4, 3.2, 2H), 3.50 (s, 2H), 4.65 (t, J=16.2, 8.4, 1H), 5.05 (s, 2H), 6.70-7.50 (m, Ar—H, 13H). Mass: m/z 325.

EXAMPLE 3

Preparation of N,N-DIISOPROPYL-3-(2-HYDROXY-5-METHYLPHENYL)-3-PHENYLPROPYLAMINE HYDROCHLORIDE (Formula V)

Step A: 3-(2-(BENZYLOXY)-5-METHYLPHENYL)-3-PHENYLPROPYL-4-METHYLBENZENESULFONATE (Formula IVa)

2010 ml of dichloromethane, 670 g of 3-(2-benzyloxy-5-methylphenyl)-3-phenyl propanol, and 844 ml of triethyl amine were stirred at 25-35° C. for about 10 minutes. A solution of p-toluene sulphonyl chloride (462 g) in dichloromethane (1340 ml) was added slowly to the reaction mass and the mixture was stirred at 25-35° C. for about 10-12 hours. A solution of 335 ml of 36% aqueous hydrochloric acid and 3015 ml of water was added to the reaction mass and stirred for 20-25 minutes. Organic layer was separated and washed with water (2×3350 ml). Distilled the solvent from the organic layer under a vacuum of about 600 mm Hg below 45° C., and the residue was dissolved in 4900 ml of acetonitrile.

Step B: N,N-DIISOPROPYLAMINE-3-(2-BENZYLOXY-5-M ETHYLPHENYL)-3-PHENYLPROPYLAMINE (Formula IVb)

The acetonitrile solution of Step A was transferred to an autoclave, 1412 ml of diisopropyl amine was added, the autoclave was sealed, and the contents were heated to 110-115° C., generating a pressure of about 2.0-3.0 kg/cm$^2$ for about 12-14 hours. Distilled the solvent from the reaction mass at 80-85° C. under vacuum of about 600 mm Hg. 4900 ml of toluene was added to the residue followed by adding 2940 ml of water and stirring for 20-30 minutes at 25-30° C. 98 ml of 36% aqueous hydrochloric acid was added to the reaction solution, stirred for 20-25 minutes and the organic layer was separated. Organic layer was washed with a solution of sodium hydroxide (82 g) in water (1960 ml) followed by washing with water (2×4900 ml). Solvent was distilled from the organic layer under a vacuum of about 600 mm Hg below 100° C. The obtained residue was dissolved in 4020 ml of methanol at 4045° C.

Step C: N,N-DIISOPROPYL-3-(2-HYDROXY-5-METHYLPHENYL)-3-PHENYLPROPYLAMINE HYDROCHLORIDE (Formula V)

The methanol solution of Step B was transferred to an autoclave, 120 ml of Raney nickel and 360 ml of water were added to the reaction solution, and a hydrogen pressure of 5-5.5 kg/cm$^2$ was applied at 25-35° C. for about 3-6 hours. Filtered the reaction mass and washed the solids with 1608 ml of methanol. pH of the filtrate was adjusted to 1-2 with 112 ml of 36% aqueous hydrochloric acid and stirred for 15-20 minutes. Distilled the solvent under a vacuum of about 600 mm Hg and the residue was dissolved in 4020 ml of dichloromethane at 40-45° C., followed by adding 4020 ml of acetone and distilling the solvents under a vacuum of about 600 mm Hg below 60° C. 6432 ml of acetone was added to the residue and stirred at reflux for 35-45 minutes. Cooled the contents to 10-15° C. for about 1-2 hours. Filtered the formed solid and washed with 1608 ml of acetone. The obtained solid was slurried in acetone, then filtered and dried at 60-65° C. for 3-4 hours to get 425 g of the desired title compound.

EXAMPLE 4

Preparation of Tolterodine Tartrate 49.2 g of sodium hydroxide flakes (NaOH) were charged into a round bottom flask containing 4920 ml of water with stirring. Cooled the solution to 25-35° C. and charged 4100 ml of dichloromethane (DCM). 410 g of N,N-diisopropyl-3-(2-hydroxy-5-methylphenyl)-3-phenylpropylamine hydrochloride from Example 3 was added and stirred for 5-10 minutes. Separated the aqueous layer and extracted with 410 ml of DCM. Combined organic layers were washed with 4100 ml of water. Separated the organic layer and distilled the solvent completely under vacuum (about 600 mm Hg) below 45° C. Charged a mixture of methanol (1950 ml) and acetonitrile (1950 ml) to the residue and stirred for 5-10 minutes. Charged 195 g of L-(+)-tartaric acid to the solution and heated to reflux. Stirred at reflux for 1-2 hours and then cooled to 0-5° C. Stirred for 1-2 hours, filtered the solid and washed with 390 ml of acetonitrile.

The wet solid thus obtained was dissolved in a mixture of NaOH (42 g) in water (2665 ml) and DCM (2460 ml) under stirring for 10-15 minutes. Separated the aqueous layer and extracted with 246 ml of DCM. Combined organic layers were washed with 2255 ml of water. Separated the organic layer and distilled the solvent completely under vacuum (about 600 mm Hg) below 45° C. Charged a mixture of methanol (740 ml) and acetonitrile (740 ml), to the residue and stirred for 5-10 minutes. Charged 74 g of L-(+)-tartaric acid to the solution and heated to reflux. Stirred at reflux for 1-2 hours and then cooled to 0-5° C. Stirred for 1-2 hours, filtered the solid and washed with 74 ml of acetonitrile.

The wet solid thus obtained was dissolved again in a mixture of NaOH (36 g), in water (2050 ml) and DCM (1845 ml) under stirring for 10-15 minutes. Separated the aqueous layer and extracted with 184 ml of DCM. Combined organic layers were washed twice with a total of 2520 ml of water. Separated the organic layer and distilled the solvent completely under vacuum (about 600 mm Hg) below 45° C. Charged acetonitrile (500 ml) to the residue and stirred for 5-10 minutes. Filtered to remove undissolved solids and washed the solids with 100 ml of acetonitrile. Filtrate was charged to a flask and a solution of 60 g of L-(+)-tartaric acid dissolved in 600 ml of methanol was added. Heated the contents to reflux and stirred at reflux for 1-2 hours. Cooled to 25-35° C. and stirred for 1-2 hours. Filtered the solid and washed with 60 ml of acetonitrile. Dried the solid at 45-50° C. under a vacuum of about 600 mm Hg for 4-5 hours to get 129 g of the title compound. (Purity: 99.98% by HPLC)

EXAMPLE 5

Preparation of BIS-[3-(2-BENZYLOXY-5-METH-YLPHENYL)-3-PHENYLPROPYL]ISOPROPY-LAMINE (Formula VI)

A mixture of 3-(2-(benzyloxy)-5-methylphenyl)-3-phenylpropyl-4-methylbenzenesulfonate of Formula IVa (120 g) and N-isopropyl-3-(2-benzyloxy-5-methylphenyl)-3-phenylpropylamine (92 g) in dimethylsulfoxide (600 ml) was heated at 60-70° C. for 18-20 hours. The reaction mass was cooled to 25-35° C., decomposed with water (600 ml), and extracted with toluene (600 ml). The toluene layer was washed with a mixture of concentrated hydrochloric acid (60 ml) and water (606 ml). The organic layer was then washed with 10% sodium hydroxide solution (240 ml), followed by water (600 ml). The organic layer was distilled completely to obtain the title compound as a syrup. Yield: 128 g (75.4%).

$^1$H NMR (200 MHz, CDCl$_3$, δ in ppm): 0.97 (d, J=6.8, 3H), 1.1 (d, J=7.4, 3H), 2.1 (s, 6H), 2.4 (t$_e$, 4H), 2.7 (m$_e$, 4H), 2.98 (m$_e$, 2H), 3.5 (m$_e$, 1H), 4.39 (t, J=15.0, 8.0, 2H), 5.00 (s, 2H), 6.6-7.1 (m, Ar—H, 26H). Mass: m/z 687.

EXAMPLE 6

Preparation of 2-(3-{[3-(2-BENZYLOXY-5-METH-YLPHENYL)-3-PHENYLPROPYL]ISOPROPY-LAMINO}-1-PHENYLPROPYL)-4-METHYLPHE-NOL (Formula VII)

A mixture of N-isopropyl-3-(2-hydroxy-5-methylphenyl)-3-phenylpropylamine (59 g) and 3-(2-(benzyloxy)-5-methylphenyl)-3-phenylpropyl-4-methylbenzenesulfonate of Formula IVa (100 g) in acetonitrile (595 ml) was heated in an autoclave at 110-115° C. for 16-18 hours. The reaction mass was cooled to 60-65° C., and solvent was distilled completely under vacuum. Charged ethyl acetate (290 ml) and water (590 ml) to the residue. Separated the aqueous layer and extracted with 118 ml of ethyl acetate. Combined organic layers were washed with water (590 ml) and distilled completely to obtain 108 g of syrup. This syrup was loaded onto a silica gel column and eluted with 5% ethyl acetate in chloroform. Distilled the solvent completely to get 38 g of the title compound as syrup.

$^1$H NMR (200 MHz, CDCl$_3$, δ in ppm): 1.10 (d, J=5.6, 3H), 1.15 (d, J=6.2,3H), 2.10 (s, 6H), 2.30 (t, J=3.2, 3.4, 4H), 2.80 (br q, 4H), 3.55 (m, 1H), 4.30 (br t, 2H), 5.05 (s, 2H), 6.6-7.1 (m, Ar—H, 21H), 7.40 (s, 1H). Mass: m/z 597.

EXAMPLE 7

Preparation of [3-(2-BENZYLOXY-5-M ETHYLPHENYL)-3-PHENYLPROPYL] ISOPROPYLAMINE (Formula VIII)

A mixture of 3-(2-(benzyloxy)-5-methylphenyl)-3-phenylpropyl-4-methylbenzenesulfonate of Formula IVa (40 g), isopropylamine (20 ml), and acetonitrile (200 ml) was stirred at 35-40° C. for 12 hours. The reaction mass was distilled completely, and the obtained residue was crystallized from ethyl acetate (280 ml) to give 28 g of the title compound as a white crystalline powder. Melting point: 137-139° C.

$^1$H NMR (200 MHz, CDCl$_3$, δ in ppm): 1.3 (d$_e$, 6H), 2.18 (s, 3H), 2.51 (q, J=23.4, 7.6, 2H), 3.18 (t, J=12.8, 6.4, 2H), 4.11 (m, 1H), 4.38 (t, J=15.8, 8.0, 1H), 5.00 (s, 2H), 6.7-7.4 (m, Ar—H, 13H), 8.7 (s, 1H). Mass: m/z 373.

We claim:
1. A process for preparing tolterodine, comprising reacting methyl 3-(2-benzyloxy-5-methyl phenyl)-3-phenylpropionate with a reducing agent to form 3-(2-benzyloxy-5-methylphenyl)-3-phenylpropanol.

2. A process for preparing tolterodine, comprising reacting 3-(2-benzyloxy-5-methylphenyl)-3-phenylpropanol with an agent providing an alkyl or arylsulfonyloxy protecting group, then reacting a protected 3-(2-benzyloxy-5-methylphenyl)-3-phenylpropanol with an aminating agent.

3. A process for preparing tolterodine, comprising:
   a) reacting methyl 3-(2-benzyloxy-5-methylphenyl)-3-phenylpropionate with a reducing agent to form 3-(2-benzyloxy-5-methylphenyl)-3-phenylpropanol;
   b) reacting 3-(2-benzyloxy-5-methylphenyl)-3-phenylpropanol with an agent providing an alkyl or arylsulfonyloxy protecting group, then reacting a protected 3-(2-benzyloxy-5-methylphenyl)-3-phenylpropanol with an aminating agent, and debenzylating to form N, N-diisopropyl-3-(2-hydroxy-5-methylphenyl)-3-phenylpropylamine hydrochloride; and
   c) reacting N, N-d iisopropyl-3-(2-hydroxy-5-methylphenyl)-3-phenylpropylamine hydrochloride with a base.

4. The process of claim 3, wherein the protected 3-(2-benzyloxy-5-methylphenyl)-3-phenylpropanol is not isolated.

5. The process of claim 3, wherein a product of reacting a protected 3-(2-benzyloxy-5-methylphenyl)-3-phenylpropanol with an aminating agent is not isolated.

6. The process of claim 3, wherein neither of the protected 3-(2-benzyloxy-5-methylphenyl)-3-phenylpropanol nor a product of reacting a protected 3-(2-benzyloxy-5-methylphenyl)-3-phenylpropanol with an aminating agent is isolated.

7. A compound methyl 3-(2-benzyloxy-5-methylphenyl)-3-phenylpropionate.

8. A compound bis-[3-(2-benzyloxy-5-methylphenyl)-3-phenylpropyl]isopropylamjne.

9. A compound 2-(3-{[3-(2-benzyloxy-5-methyl phenyl)-3-phenylpropyl]isopropylamino}-1 -phenylpropyl)-4-methylphenol.

10. A compound [3-(2-benzyloxy-5-methylphenyl)-3-phenylpropyl]isopropylamine.

* * * * *